United States Patent
Nitz et al.

(10) Patent No.: US 9,878,979 B2
(45) Date of Patent: Jan. 30, 2018

(54) FINE PURIFICATION OF ISOPHORONENITRILE BY MELT CRYSTALLIZATION

(71) Applicants: Joerg-Joachim Nitz, Essen (DE); Stephan Kohlstruk, Gladbeck (DE); Robert Jansen, Bottrop (DE); Anja Mueller, Dortmund (DE); Jan Cassens, Recklinghausen (DE); Axel Hengstermann, Senden (DE)

(72) Inventors: Joerg-Joachim Nitz, Essen (DE); Stephan Kohlstruk, Gladbeck (DE); Robert Jansen, Bottrop (DE); Anja Mueller, Dortmund (DE); Jan Cassens, Recklinghausen (DE); Axel Hengstermann, Senden (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/361,223

(22) Filed: Nov. 25, 2016

(65) Prior Publication Data
US 2017/0152217 A1    Jun. 1, 2017

(30) Foreign Application Priority Data

Nov. 30, 2015  (EP) ..................................... 15196938

(51) Int. Cl.
*C07C 253/34*  (2006.01)

(52) U.S. Cl.
CPC .................................. *C07C 253/34* (2013.01)

(58) Field of Classification Search
None
See application file for complete search history.

(56) References Cited

U.S. PATENT DOCUMENTS

| | | |
|---|---|---|
| 5,011,968 A | 4/1991 | Thunberg et al. |
| 5,504,247 A | 4/1996 | Saxer et al. |
| 5,831,124 A | 11/1998 | Machhammer et al. |
| 2003/0166947 A1 | 9/2003 | Eck et al. |

FOREIGN PATENT DOCUMENTS

| | | | |
|---|---|---|---|
| CN | 101851178 A | | 10/2010 |
| CN | 102020586 A | * | 4/2011 |
| CN | 102199109 A | | 9/2011 |
| EP | 0 616 998 A1 | | 9/1994 |
| EP | 0 792 867 A2 | | 9/1997 |
| EP | 0 792 867 A3 | | 9/1997 |
| WO | WO 01/90066 A2 | | 11/2001 |
| WO | WO 01/90066 A3 | | 11/2001 |

OTHER PUBLICATIONS

European Search Report dated May 18, 2016 in European Patent Application No. 15196938.3 (with English translation of categories of cited documents).
P. J. Jansens et al. "Melt Crystallization" Encyclopedia of Separation Science Level II, XP55269551, 2000 (pp. 966-975).

* cited by examiner

*Primary Examiner* — Michael Barker
(74) *Attorney, Agent, or Firm* — Oblon, McClelland, Maier & Neustadt, L.L.P.

(57) ABSTRACT

The present invention relates to the fine purification of isophoronenitrile (IPN) by melt crystallization.

9 Claims, 2 Drawing Sheets

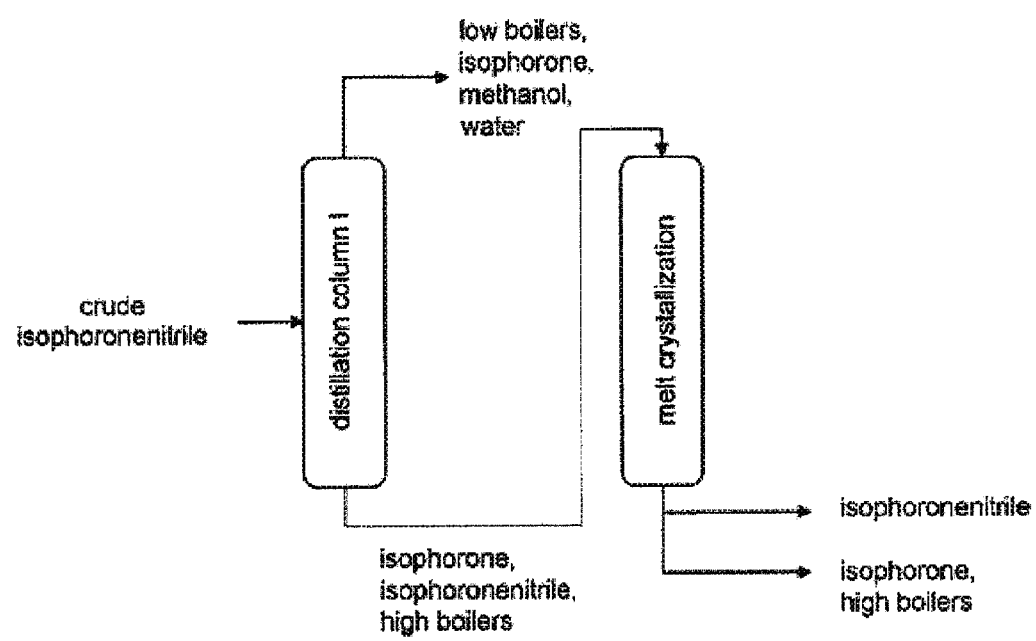
Figure 1: Schematic representation of the final purification step with distillation and melt crystallization (variant 1)

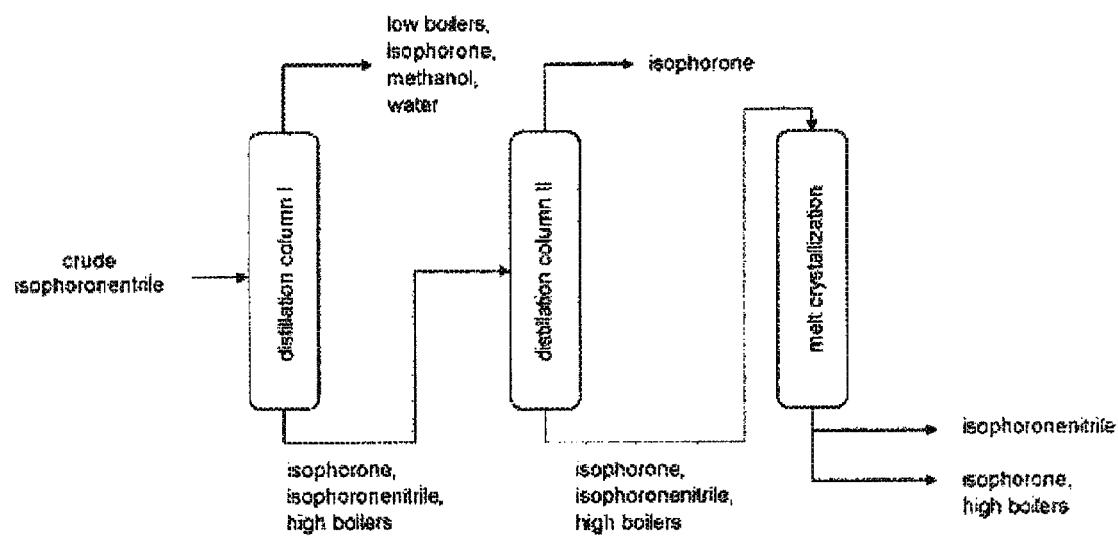
Figure 2: Schematic representation of the final purification step with two distillations and melt crystallization (variant 2)

_US 9,878,979 B2_

FINE PURIFICATION OF ISOPHORONENITRILE BY MELT CRYSTALLIZATION

BACKGROUND OF THE INVENTION

The present invention relates to the fine purification of isophoronenitrile (IPN) by melt crystallization.

FIELD OF THE INVENTION

The base-catalyzed reaction of hydrocyanic acid (HCN) with alpha,beta-unsaturated cyclic (or acyclic) ketones is a known reaction (Hydrocyanation of Conjugated Carbonyl Compounds, CHAPTER 3, Wataru Nagata and Mitsuru Yoshioka, Wiley 2005).

EP 2 721 002 discloses numerous processes for producing isophoronenitrile, see the documents cited therein.

Isophoronenitrile (IPN) is formed by reaction of isophorone (IP) with hydrocyanic acid with the aid of a catalyst. It is preferable to employ homogeneous base catalysis, alkali metal alkoxides, in particular sodium methoxide, being used as catalyst to this end.

Isophoronenitrile is produced by reaction of hydrogen cyanide (HCN) and isophorone (IP) in the presence of sodium methoxide as catalyst as is described in EP 2649043. The product mixture formed in this reaction comprises not only the product isophoronenitrile hut also the unconverted reactants hydrogen cyanide and isophorone and also the catalyst, methanol and residues. This product mixture is purified by distillation in a multistage process, the isophoronenitrile being obtained in pure form in the final stage. This can achieve purities of at least 99.8 wt %. This purified isophoronenitrile is converted into isophoronediamine in a further reaction. However, the small amounts of impurities still present in the purified isophoronenitrile can have a deleterious effect on the lifetime of the catalyst used in isophoronediamine production and can reduce the color stability of the isophoronediamine.

SUMMARY OF THE INVENTION

The present invention has for its object to improve the workup of the product mixture composed of isophoronenitrile, the unconverted reactants hydrogen cyanide and isophorone and also the catalyst, methanol and residues.

It has now been found that, surprisingly, a melt crystallization downstream of the distillation can enhance the purity of the isophoronenitrile and thus remove disruptive impurities.

BRIEF DESCRIPTION OF THE DRAWINGS

FIG. 1 shows a schematic representation of the final purification step with distillation and melt crystallization (variant 1).

FIG. 2 shows a schematic representation of the final purification step with two distillations and melt crystallization (variant 2).

DETAILED DESCRIPTION OF THE INVENTION

The invention provides a process for purifying isophoronenitrile from the production of isophoronenitrile from isophorone and hydrocyanic acid in the presence of a catalyst, characterized in that the removal of impurities in the isophoronenitrile is effected via a melt crystallization.

In accordance with the invention the workup of the product mixture, composed essentially of isophoronenitrile, the unconverted reactants hydrogen cyanide and isophorone and also the catalyst, methanol and residues, is effected by inch crystallization where impurities in the isophoronenitrile which were not able to be removed in the distillation are removed.

In the industrial-scale reaction the crystallization of the isophoronenitrile may be carried out as a suspension crystallization or as a layer crystallization.

Layer crystallization in particular lends itself to the present separation problem. The layer crystallization may be carried out either in static operation or in dynamic operation, a combination of both process steps being preferred.

After crystallization has ended the mother liquor is discharged and introduced into a sweating process. Said process may have a duration between 1 minute up to 20 minutes. After discharge of the sweated fraction the crystallizate may be melted off and subjected to further processing. The crystallization may be carried out in one stage or preferably in a plurality of stages, wherein in the multistage variant the discharged mother liquor and the sweated fraction and also the crystallizate are collected in different buffering containers. Depending on the desired purity the crystallizate is processed again. To increase yield the mother liquor and the sweated fraction are processed again.

One preferred apparatus setup for a dynamic crystallization is the falling film crystallizer where the circulating product mixture for purification is allowed to run down the wall of an externally cooled tube and thus begins to crystallize on the tube wall. The length of this tube may be from 2 m up to 16 m. It is additionally possible to achieve higher throughputs by employing a plurality of tubes as a tube bundle, a distributor ensuring uniform application of the film consisting of the product mixture for purification in each of the tubes.

A static crystallization may be run in a falling film crystallizer even without circulation but is preferably carried out in a plate crystallizer.

Description of the Preferred Embodiment for Purification of Isophoronenitrile by Means of Melt Crystallization (Variant 1)

The product mixture composed of isophoronenitrile, the unconverted reactants hydrogen cyanide and isophorone and also the catalyst, methanol and residues is initially worked up by distillation in a first column to remove all of the water, low boilers and methanol and to remove more than 85% of the isophorone. In a first variant a distillation is simultaneously carried out to remove the water, the likewise removed isophorone being condensed out by means of a particle condenser and recycled into the reaction. The IPN/IP mixture exiting from the column-bottom is subsequently passed into the melt crystallization apparatus (FIG. 1). The above-described procedure is then followed after crystallization has ended.

The invention accordingly further provides a process for purifying isophoronenitrile by melt crystallization, wherein the product mixture composed essentially of isophoronenitrile, the unconverted reactants hydrogen cyanide and isophorone and also the catalyst, methanol and residues is purified as follows:

I. purification of the product mixture by a distillation by
1. removal of water, low boilers and methanol and also at least 85% of the isophorone at the top of the column, the isophorone proportion being condensed by means of a partial condenser and recycled into the reaction,
2. removal in the bottom of the column of isophoronenitrile and the remaining isophorone and impurities (high boilers);

II. the mixture from 1.2. accumulating in the column-bottom is sent to a melt crystallization to remove the impurities and isolate the isophoronenitrile.

Description of the Preferred Embodiment for Purification of Isophoronenitrile by Means of Melt Crystallization (Variant 2)

The product mixture composed of isophoronenitrile, the unconverted reactants hydrogen cyanide and isophorone and also the catalyst, methanol and residues is initially worked up by distillation in a first column to remove water, low boilers, methanol and some, preferably not more than 10%, of the isophorone. This is followed by a further distillation of the isophoronenitrile impurified with isophorone and high boilers which is obtained from the bottom of the first column. The distillation in the second column is used to remove pure isophorone at the top of the column, the isophoronenitrile impurified with residual isophorone (no more than 15 wt %) and high boilers being withdrawn hi the bottom of the column and sent to a melt crystallization (FIG. 2). The abovedescribed procedure is then followed after crystallization has ended.

The invention accordingly further provides a process for purifying isophoronenitrile by melt crystallization, wherein the product stream from the reaction reactor for producing isophoronenitrile composed essentially of isophorone, hydrocyanic acid and catalyst, crude isophoronenitrile, is purified as follows:

I. Purification of the Product Stream by a First Distillation
   a) to remove water, low boilers, methanol and some, preferably not more than 10%, of the isophorone at the top of the column,
   and
   b) removal in the bottom of the column of isophoronenitrile and the remaining isophorone and impurities (high boilers);

II. purification of the product stream from I. b) in a second distillation column and removal of the isophoronenitrile, isophorone and impurities from the bottom of the column;

III. the mixture from II accumulating in the column-bottom is sent to a melt crystallization to remove the impurities and isolate the isophoronenitrile.

Having generally described this invention, a further understanding can be obtained by reference to certain specific examples which are provided herein for purposes of illustration only, and are not intended to be limiting unless otherwise specified.

EXAMPLES

This purification process was investigated using a falling film crystallizer having a descending tube of 2 m in length. The crude product transferred into the crystallizer is frozen out in a vertical externally cooled descending tube on the tube wall. The impurities remaining in the mother liquor are then discharged and the crystallizate is melted off and discharged as pure product. As a further purification step a sweating procedure was initiated after crystallization.

Crude isophoronenitrile was withdrawn from the existing process upstream of the final purification step to serve as medium. An isophoronenitrile mixture impurified with residues was thus used. This mixture was employed both in pure form and with artificially added isophorone (total isophorone content 12.5 wt %).

Having generally described this invention, a further understanding can be obtained by reference to certain specific examples which are provided herein for purposes of illustration only, and are not intended to be limiting unless otherwise specified.

Example 1—Variant 1

A crude isophoronenitrile was crystallized as a feed in a static mode of operation (cooling medium up to 40° C.), wherein the crystallization space was filled with feed and then a crystallization from the mother liquor in the descending tube was carried out, After discharging of the mother liquor a sweating process at 67° C. was initiated to remove further impurities from the crystallizate. Each of the fractions was sampled and the isophoronenitrile proportion thereof determined. The results are reported in table 1 and it is apparent here that the isophoronenitrile purity can be increased from 98.2 to 99.3 wt %.

TABLE 1

| Isophoronenitrile concentrations after static crystallization in the individual fractions | | |
|---|---|---|
| feed concentration | 98.2 | wt % |
| concentration in mother liquor | 97.2 | wt % |
| concentration in crystallizate | 99.3 | wt % |

Example 2—Variant 2

The purification of a feed solution of crude isophoronenitrile having an IP proportion of 13.2 wt % was investigated. For the crystallization the crystallizer was operated in a dynamic mode, wherein the mother liquor was recycled in a continuous circulation from the bottom of the crystallizer via a riser conduit into the top of the crystallizer. The crystallizate was frozen out of the mother liquor flowing back via the descending tube as a film (cooling medium up to 40° C.). After discharging of the mother liquor a sweating process at 67° C. was initiated to remove further impurities from the crystallizate. Each of the fractions was sampled and the isophoronenitrile proportion thereof determined. The results are reported in table 2. Here too an improvement in purity was achieved which also showed that isophoronenitrile may be selectively separated from isophorone by crystallization.

TABLE 2

| Isophoronenitrile concentrations after dynamic crystallization in the individual fractions | | |
|---|---|---|
| feed concentration | 85.9 | % by wt. |
| concentration in mother liquor | 83.1 | % by wt. |
| concentration in crystallizate | 93.8 | % by wt. |

European patent application 15196938.3 filed Nov. 30, 2015, is incorporated herein by reference. Numerous modifications and variations on the present invention are possible in light of the above teachings. It is therefore to be understood that within the scope of the appended claims, the invention may be practiced otherwise than as specifically described herein.

The invention claimed is:

1. Process for purifying isophoronenitrile from the production of isophoronenitrile from isophorone and hydrocyanic acid in the presence of a catalyst, characterized in that the removal of impurities in the isophoronenitrile is effected by melt crystallization.

2. Process for purifying isophoronenitrile according to claim 1, wherein the melt crystallization is effected by suspension crystallization or by layer crystallization.

3. Process for purifying isophoronenitrile according to claim 1, wherein the melt crystallization is carried out as a layer crystallization in static operation or in dynamic operation or a combination of both process steps.

4. Process for purifying isophoronenitrile according to claim 1, wherein the melt crystallization is carried out in one stage or in a plurality of stages.

5. Process for purifying isophoronenitrile according to claim 1, wherein the melt crystallization is carried out in a plurality of stages and wherein the discharged mother liquor and the sweated fraction and also the crystallizate are collected in different buffering containers.

6. Process for purifying isophoronenitrile according to claim 1, wherein the dynamic melt crystallization is carried out in at least one falling film crystallizer.

7. Process for purifying isophoronenitrile according to claim 1, wherein the static melt crystallization is carried out in at least one falling film crystallizer or in an at least one plate crystallizer.

8. Process for purifying isophoronenitrile by melt crystallization according to claim 1, wherein the product mixture composed essentially of isophoronenitrile, the unconverted reactants hydrogen cyanide and isophorone and also the catalyst, methanol and residues is purified as follows:

I. purification of the product mixture by a distillation by
  1. removal of water, low boilers and methanol and also at least 85% of the isophorone at the top of the column, the isophorone proportion being condensed by means of a partial condenser and recycled into the reaction,
  2. removal in the bottom of the column of isophoronenitrile and the remaining isophorone and impurities (high boilers);
II. the mixture from I.2. accumulating in the column-bottom is sent to a melt crystallization to remove the impurities and isolate the isophoronenitrile.

9. Process for purifying isophoronenitrile by melt crystallization according to claim 1, wherein the product stream from the reaction reactor for producing isophoronenitrile composed essentially of isophorone, hydrocyanic acid and catalyst, crude isophoronenitrile, is purified as follows:

I. purification of the product stream by a first distillation
  a) to remove water, low boilers, methanol and some, preferably not more than 10%, of the isophorone at the top of the column,
and
  b) removal in the bottom of the column of isophoronenitrile and the remaining isophorone and impurities (high boilers);
II. purification of the product stream from I. b) in a second distillation column and removal of the isophoronenitrile, isophorone and impurities from the bottom of the column;
III. the mixture from II accumulating in the column-bottom is sent to a melt crystallization to remove the impurities and isolate the isophoronenitrile.

* * * * *